(12) United States Patent
Petersen

(10) Patent No.: US 6,849,749 B2
(45) Date of Patent: Feb. 1, 2005

(54) METHOD FOR THE PREPARATION OF CITALOPRAM

(75) Inventor: Hans Petersen, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/977,920

(22) Filed: Oct. 15, 2001

(65) Prior Publication Data

US 2002/0040153 A1 Apr. 4, 2002

Related U.S. Application Data

(63) Continuation of application No. PCT/DK99/00210, filed on Apr. 14, 1999.

(51) Int. Cl.$^7$ .................... C07D 307/78; C07D 307/87; C07D 307/93; A61K 31/34
(52) U.S. Cl. ........................................ 549/467; 514/469
(58) Field of Search .......................... 549/467; 514/469

(56) References Cited

U.S. PATENT DOCUMENTS

| | | | |
|---|---|---|---|
| 4,136,193 A | * 1/1979 | Bogeso et al. | |
| 6,162,942 A | 12/2000 | Rock et al. | 558/337 |
| 6,310,222 B1 | 10/2001 | Ikemoto et al. | 549/467 |
| 6,331,628 B1 | 12/2001 | Kondo et al. | 544/312 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,426,422 B1 | 7/2002 | Petersen et al. | 549/467 |
| 6,433,196 B1 | 8/2002 | Ikemoto et al. | 549/469 |
| 2002/0026062 A1 | 2/2002 | Petersen et al. | 549/467 |
| 2002/0087012 A1 | 7/2002 | Castellin et al. | |
| 2002/0120005 A1 | 8/2002 | Villa et al. | |
| 2002/0128497 A1 | 9/2002 | Bolzonella et al. | |
| 2002/0198391 A1 | 12/2002 | Petersen et al. | |
| 2003/0013895 A1 | 1/2003 | Petersen | |
| 2003/0050484 A1 | 3/2003 | Petersen | |
| 2003/0060640 A1 | 3/2003 | Petersen | |
| 2003/0060641 A1 | 3/2003 | Petersen et al. | |
| 2003/0069304 A1 | 4/2003 | Petersen | |
| 2003/0078442 A1 | 4/2003 | Petersen et al. | |
| 2003/0083508 A1 | 5/2003 | Petersen et al. | |
| 2003/0083509 A1 | 5/2003 | Petersen et al. | |
| 2003/0092761 A1 | 5/2003 | Rock et al. | |
| 2003/0092919 A1 | 5/2003 | Petersen | |

FOREIGN PATENT DOCUMENTS

| | | | |
|---|---|---|---|
| WO | WO 98/19513 | * | 5/1998 |
| WO | WO 01/02383 A2 | | 1/2001 |
| WO | WO 01/85712 A1 | | 11/2001 |
| WO | WO 03/011278 | | 2/2003 |

OTHER PUBLICATIONS

Harrison et al., Compendium of Organic Synthetic Methods, 1971 pp. 148 and 461.*
Huber, Vincent J. et al., "Preparation of Nitriles from Carboxylic Acids: A New, Synthetically Useful Examples of the Smiles Rearrangement," *Tetrahedron* 54: 9281–9288 (1998).
Buehler, Calvin A. et al., *Survey of Organic Synthesis*: 951, New York: Wiley–Interscience (1979).
U.S. Appl. No. 09/930,107, filed Aug. 14, 2001.
Levy, L.F., "4–Aminophthalide and Some Derivatives", *J. Chem. Soc.* pp. 867–870, (1931).
Tirouflet J., "Phtalide Substitutes en 5", *Bull. Soc. Sci. de Bretagne*, 26:35–43 (1951).
Bigler et al., "Quantitive structure–activity relationships in a series of selective 5–HT uptake inhibitors," *Eur. J. Med. Chem.* 12, 3: 289–295 (1997).
U.S. Appl. No. 09/794,762, filed Feb. 26, 2001.
U.S. Appl. No. 09/794,755, filed Feb. 26, 2001.
U.S. Appl. No. 09/830,109, filed Jun. 1, 2001, (International filing date).
U.S. Appl. No. 09/888,067, filed Dec. 22, 1999 (International filing date).
U.S. Appl. No. 09/891,874, filed Oct. 25, 1999, (International filing date).
U.S. Appl. No. 09/917,180, filed Jan. 26, 2000, (International filing date).
U.S. Appl. No. 09/692,653, filed Oct. 18, 2000.
U.S. Appl. No. 09/930,107, filed Aug. 14 , 2001.
U.S. Appl. No. 09/930,110, filed Aug. 14 , 2001.
Levy, L.F., "4–Aminophthalide and Some Derivatives", *J. Chem. Soc*, pp. 867–870, (1931).
Tirouflet J., "Phtalide Substitutes en 5", *Bull. Soc. Sci. de Bretagne*, 26:35–43 (1951).
Perregaard, Jens et al., "σ Ligands with Subnanomolar Affinity and Preference for the $\sigma_2$ Binding Site 1. 3–(ω–Aminoalkyl)–1 H–indoles," *J. Med. Chem.* 38:1998–2008 (1995.

* cited by examiner

*Primary Examiner*—Shengjun Wang
(74) *Attorney, Agent, or Firm*—Darby & Darby

(57) ABSTRACT

A method for the preparation of citalopram comprising reductive hydrolysis of a compound of Formula (IV):

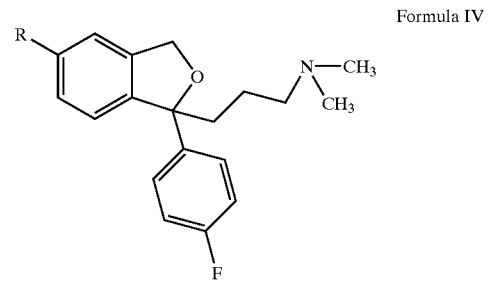

Formula IV wherein R is a N,N-disubstituted amid group or an optionally substituted 4,5-dihydro-1,3-oxazol-2-yl group, and conversion of the resulting 5-formyl compound to citalopram.

21 Claims, No Drawings

METHOD FOR THE PREPARATION OF CITALOPRAM

This is a continuation of International application Ser. No. PCT/DK99/00210, filed 14 Apr. 1999, the entire disclosure of which is hereby incorporated by reference.

The present invention relates to a method for the preparation of the well known anti-depressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

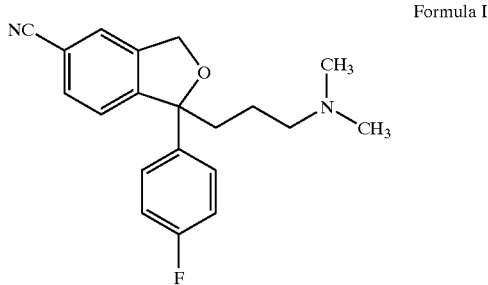

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

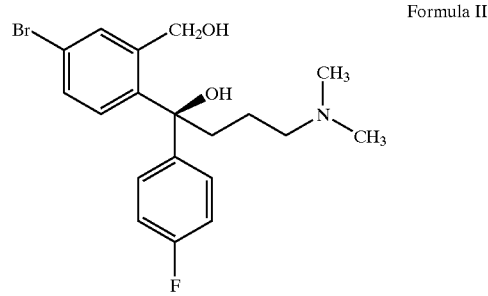

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula:

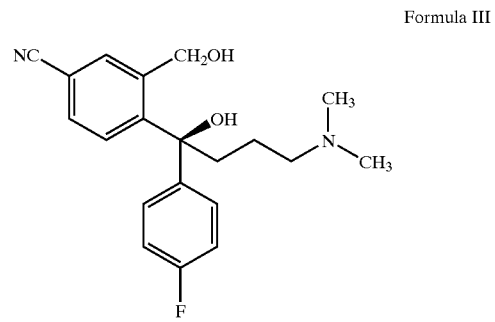

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98019511, WO 98019512 and WO 98019513. WO 98019512 and WO 98019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorphenyl)methanol compound is subjected to ring closure and the resulting 5-substituted 1-(4-fluorophenyl)-1,3-dihydroisobenzofuran converted to the corresponding 5-cyano derivative which is alkylated with a (3-dimethylamino) propylhalogenide in order to obtain citalopram.

Finally, methods of preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising the steps of:

a) subjecting a compound of Formula IV:

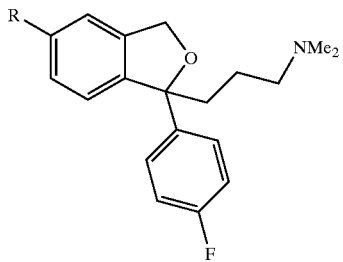

Formula IV wherein R is a group

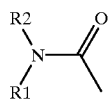

wherein R1 and R2 are independently selected from lower alkyl, aryl and heteroaryl, or R1 and R2 are linked and together designate a 4- or 5-membered chain optionally comprising an S, O or N atom, or 4,5-dihydro-1,3-oxazol-2-yl optionally substituted in the 4- and/or 5-position with one ore more lower alkyl, aryl or heteroaryl groups to reductive hydrolysis, and b) converting the resulting 5-formyl compound of Formula V:

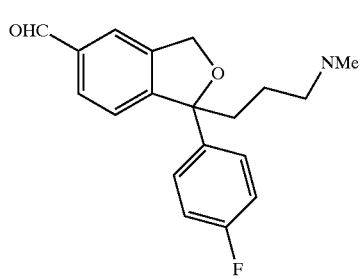

Formula V to the corresponding 5-cyano compound, i.e. citalopram:

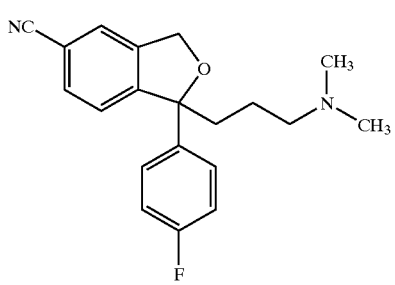

Formula I which is isolated as the base or a pharmaceutically acceptable salt thereof.

In another aspect, the present invention provides the novel intermediate of Formula V.

A further aspect of the invention relates to the novel intermediate for preparation of citalopram having Formula IV.

In a further aspect the invention relates to the above process in which the compound of Formula IV is the S-enatiomer.

In yet another aspect, the present invention relates to an antidepressant pharmaceutical composition comprising citalopram manufactured by the process of the invention.

Throughout the specification and claims, lower alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl- 1-ethyl and 2-methyl-1-propyl.

The term aryl refers to a mono- or bicyclic carbocyclic aromatic group, such as phenyl and naphthyl, in particular phenyl.

The term heteroaryl refers to a mono- or bicyclic heterocyclic aromatic group, such as indolyl, thienyl, pyrimidyl, oxazolyl, isoxazolyl, thiazolyl, isothiazolyl, imidazolyl, benzofuranyl, benzothienyl, pyridyl, and furanyl, in particular pyrimidyl, indolyl, and thienyl.

Halogen means fluoro, chloro, bromo or iodo.

Reductive hydrolysis means reduction of the group R followed by treatment with $H_2O$ thereby forming an aldehyde group.

When R1 and R2 are linked and together designate a 4- or 5-membered chain optionally comprising an S, O or N atom, R1 and R2 together with the N-atom to which they are linked form a 5- or 6-membered ring optionally having a heteroatom selected from O, S and N in addition to the N-atom to which R1 and R2 are linked. Examples of such groups are morpholinyl, piperidyl, etc.

In a preferred embodiment of the invention, R is morpholinocarbonyl, di(lower alkyl)aminocarbonyl or 4,4-di(lower alkyl)-1,3-oxazolidin-2-yl, most preferably morpholinocarbonyl, dimethylaminocarbonyl or 4,4-dimethyl-1,3-oxazolidin-2-yl.

In a preferred embodiment of the invention the intermediate of Formula IV is prepared by ring closure of the corresponding compound of Formula VI:

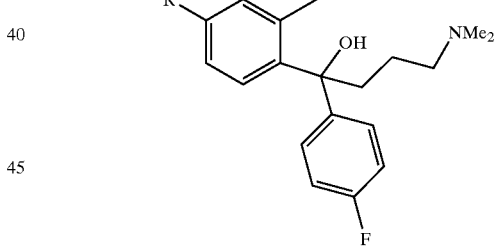

Formula VI

Preferably the compound of Formula VI is obtained from the corresponding 5-R-substituted phthalide derivative by two successive Grignard reactions, i.e. with a Grignard reagent of 4-halogen-fluorophenyl and a Grignard reagent of 3-halogen-N,N-dimethyl-propylamine, respectively. When R is an optionally substituted 4,5-dihydro-1,3-oxazol-2-yl group the compound of Formula VI may alternatively be prepared from 4-dimethylamino-1-(4-fluorophenyl)-butan-1-one by Grignard reaction with a properly protected 2-(hydroxymethyl)-4-(4,5-dihydro-1,3-oxazol-2-yl)-phenyl magnesium halogenide derivative.

The reductive hydrolysis of the compound of Formula IV is conveniently carried out by reduction of a compound of Formula IV with a suitable reducing agent such as an aluminium or boron containing agent, conveniently Dibal-H, superhydride, $LiAlH_4$, $BH_4^-$ ($Li^+$, $Na^+$ or $K^+$), etc., followed by addition of $H_2O$. When R is a 4,5-dihydro-1,3-oxazol-2-yl-group the reaction may be carried out by alkylation with a proper alkylation agent, such as MeI, a dialkylsulfate or like, followed by reduction and hydrolysis as above. In all cases the reduction is performed under strictly controlled conditions, preferably at about 0° C.

The conversion of the 5-formyl compound of Formula V to citalopram is carried out by conversion of the formyl group to an oxime or similar group by reaction with a reagent R3-X-$NH_2$ wherein R3 is hydrogen, lower alkyl, aryl or heteroaryl and X is O, N or S, followed by dehydration with a common dehydrating agent, for example thionylchloride, acetic anhydride/pyridine, pyridine/HCl or phosphor pentachloride. Preferred reagents R3-X-$NH_2$ are hydroxylamin and compounds wherein R3 is alkyl or aryl and X is N or O.

Ring closure of the compound of Formula VI may be effected by an acid or via a labile ester with a base. Acidic ring closure is performed by an inorganic acid, such as a sulfuric or phosphoric acid, or an organic acid, such as methylsulfonic, p-toluenesulfonic or trifluoroacetic acid. The basic ring closure is performed via a labile ester, such as the methane sulfonyl, p-toluene sulfonyl, 10-camphorsulfonyl, trifluoroacetyl or trifluoromethane-sulfonyl ester with addition of a base, such as triethyl amine, dimethylaniline, pyridine, etc. The reaction is performed in an inert solvent, preferably with cooling, in particular about 0° C. and is preferably carried out by a one-pot procedure, i.e. with esterification and simultaneous addition of the base. Before further reaction the intermediate of Formula VI may be separated into its enantiomers, thereby obtaining the enantiomer giving S-citalopram.

Grignard reagents of 4-halogen-fluorophenyl that may be used in the preparation of a compound of Formula VI are the magnesium halogenides, such as the chloride, bromide or iodide. Preferably the magnesiun bromide is used. Grignard reagents of 3-halogen-N,N-dimethylpropylamine that may be used are the magnesium halogenides, such as the chloride, bromide or iodide, preferably the magnesium chloride. Preferably the two reactions are performed successively without isolation of the intermediate.

Other reaction conditions, solvents, etc. are conventional conditions for such reactions and may easily be determined by a person skilled in the art.

The 5-R-substituted phthalide starting materials used in the Grignard reactions may be prepared from 5-chlorocarbonylphthalide by reaction with the proper amine compounds.

5-chlorocarbonylphthalide may again be prepared from 5-carboxyphtalide by reaction with thionyl chloride. 5-carboxyphtalide is commercially available and may be prepared by well known procedures (Tirouflet, J.; Bull.Soc-.Sci. Bretagne 26, 1959,35).

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

EXAMPLES

The invention is further illustrated by the following examples.

Example 1

5-(4-morpholylcarbonyl)phthalid

A solution of 5-chlorocarbonylphthalid (39 g, 0.2 mole) in THF (400 ml) is added to a solution of morpholine (22 g. 0.25 mole) and triethylamine (26 g, 0.25 mole) in THF (200 ml) at 0° C. The mixture is stirred for 1 hour and is allowed to warm to room temperature. The reaction mixture is then poured into ice water ( 500 ml). THF is evaporated off in vacuo and the pH of the solution is adjusted to pH=2. The solution is cooled to 5° C. and the precipitated crystals are filtered off and washed with water (100 ml).

Yield 38.0 g, 78%. DSC onset: 83° C. and 107° C. Purity: 99.6% (hplc, peak area). $^1$H NMR (DMSO-$d_6$, 250 MHz): 3.2–3.7 (8H, m), 5.45 (2H, s), 7.60 (1H, d, J=7.5 Hz), 7.72 (1H, s), 7.92 (1H, d, J=7.5 Hz). $^{13}$C NMR (DMSO-$d_6$, 62.9 MHz): 42.1, 47.7, 66.1, 70.0, 121.6, 125.3, 125.7, 127.7, 141.2, 147.7, 168.0, 170.1.

Anal. calcd. for $C_{13}H_{13}O_4N_1$; C, 63.15: H, 5.30: N, 5.66. Found C, 62.94: H, 5.52: N, 5.53.

Example 2

5-(N,N-dimethylcarbamyl)phthalid

A solution of 5-chlorocarbonylphthalid (32 g, 0.16 mole) in THF (300 ml) is added to dimethylamine (40% v/v in water, 300 ml) and ice (100 g). The mixture is stirred for 1 hour. THF is evaporated off in vacuo and precipitated crystals are filtered off at 5° C. and washed with water (100 ml).

Yield 30.0 g, 90%. DSC onset: 154° C. $^1$H NMR (DMSO-$d_6$, 250 MHz): 2.9 (3H, s), 3.03 (3H, s), 5.45 (2H, s), 7.57 (1H, d, J=7.5 Hz), 7.70 (1H, s), 7.90 (1H, d, J=7.5 Hz). $^{13}$C NMR (DMSO-$d_6$, 62.9 MHz): 34.7, 40.0, 70.0, 121.4, 125.1, 125.5, 127.6, 142.1, 147.6, 169.0, 170.1.

Anal. calcd. for $C_{11}H_{11}O_3N_1$; C, 64.38: H, 5.40: N, 6.83. Found C, 64.17: H, 5.44: N, 6.61.

Example 3
5-(1-Hydroxy-2-methylprop-2-yl)carbamylphthalid

Method A): A solution of 5-chlorocarbonylphthalid (39 g, 0.2 mole) in THF (400 ml) is added to a solution of 2-amino-2-methylpropan-1-ol (22.3 g. 0.25 mole) and triethyl-amine (26 g, 0.25 mole) in THF (200 ml) at 0° C. The mixture is stirred for 1 hour and is allowed to warm to room temperature. The reaction mixture is then poured into ice water (500 ml).THF is evaporated off in vacuo and the pH of the solution is adjusted to pH=2. The solution is cooled to 5° C. and left over night. The precipitated crystals are filtered off and washed with cold water (100 ml).

Yield 34.0 g, 68%. DSC onset: 165° C. Purity: 99.7% (hplc, peak area). $^1$H NMR (DMSO-$d_6$, 250 MHz): 1.33 (6H, s), 3.54 (2H, s), 5.47 (2H, s), 7.84 (1H,s), 7.90 (1H, d, J=7.5 Hz), 7.97 (1H, d, J=7.5 Hz), 8.03 (1H, s). $^{13}$C NMR (DMSO-$d_6$, 62.9 MHz): 23.6, 55.4, 67.2, 70.1, 122.1, 124.8, 126.7, 128.3, 141.2, 147.3, 165.8, 170.2.

Anal. calcd. for $C_{13}H_{15}O_4N_1$; C, 62.64: H, 6.07: N, 5.62. Found C, 62.37: H, 6.13: N, 5.53.

Method B): 5-Ethoxycarbonylphthalid (82 g, 0.4 mole) is added to a solution of 2-amino-2-methylpropan-1-ol (44.6 g. 0.5 mole) in toluene (100 ml). The mixture is heated to reflux temperature for 24 hours. Upon cooling the title compound is filtered off and recrystallised from hot toluene.

Yield 85.0 g, 85%. Purity: 95.0% (hplc, peak area).

Example 4
5-(4-morpholylcarbonyl)-1-(3-dimethylaminopropyl)-1-(4-fluorophenyl)-1,3-dihydroisobenzofuran, oxalate A solution of 4-fluorophenylmagnesium bromide, prepared from 4-fluorobromobenzene (31 g, 0.17 mole) and magnesium turnings (6 g, 0.24 mole) in dry THF (100 ml), is added dropwise to a suspension of 5-(4-morpholylcarbonyl)phthalid (36 g, 0.15 mole) in dry THF (150 ml). The temperature is kept below 5° C. After the addition is complete, the reaction mixture is stirred for 1.5 hours at room temperature.

A second Grignard solution prepared from 3-dimethylaminopropyl chloride (22.3 g, 0.17 mole) and magnesium turnings (6 g, 0.24 mole) in dry THF (150 ml) is added to the reaction mixture. The temperature is kept below 10° C. during the addition. The reaction is left overnight at room temperature with stirring.

The reaction mixture is poured into ice water (300 ml) and a saturated solution of ammonium chloride (100 ml). THF is evaporated off in vacuo. Dichloromethane (300 ml) is added and the organic phase is separated and washed with water (2×100 ml) and brine (50 ml). The organic phase is extracted with 2 M HCl (2×100 ml). To the aqueous phase 4 M NaOH (100 ml) is added to give a final pH of 9 or higher. The water layer is extracted with DCM (400 ml) and the organic phase is washed with water (100 ml), brine (50 ml) and dried with $MgSO_4$ (20 g).

Triethylamine (20 g, 0.2 mole) is added to the organic phase and the solution is cooled to 5° C. Methanesulfonyl chloride (12 g, 0.11 mole) in DCM (100 ml) is added dropwise and after addition the reaction mixture is left for one hour with stirring. The reaction mixture is washed with 0.1 M NaOH (2×100 ml) and the organic phase is dried ($MgSO_4$, 10 g) and the solvent is evaporated in vacuo. The thus obtained material is dissolved in acetone (100 ml) and treated with anhydrous oxalic acid (13.5 g, 0.15 mole) dissolved in acetone (100 ml). The mixture is left at room temperature overnight and the precipitated oxalate is filtered off.

Yield: 19 g, 26%. DSC onset 166 C. $^1$H NMR (DMSO-$d_6$, 250 MHz): 1.35–1.63 (2H, m), 2.20 (2H, t, J=10 Hz), 2.64 (6H, s), 2.97 (2H, t, J=10 Hz), 3.3–3.7 (8H, m), 5.13 (1H, d, J=12.5 Hz), 5.23 (1H, d, J=12.5 Hz), 7.15 (2H, t, J=8.5 Hz), 7.32 (2H, s+d, J=1.2 Hz), 7.52–7.65 (3H, t+d, J=8.5 Hz J=1.2 Hz).

Anal. calcd. for $C_{24}H_{29}N_1F_1O_3$. 1.1 $C_2H_2O_4$; C, 61.52: H, 6.15: N, 5.48. Found C, 61.53: H, 6.22: N, 5.40.

Example 5
5-(N,N-dimethylcarbamyl)-1-(3-dimethylaminopropyl)-1-(4-fluorophenyl)-1,3-dihydroisobenzofuran, oxalate A solution of 4-fluorophenylmagnesium bromide, prepared from 4-fluorobromobenzene (16.5 g, 0.09 mole) and magnesium turnings (3 g, 0.12 mole) in dry THF (50 ml), is added dropwise to a suspension of 5-N,N-dimethylcarbamylphthalid (16.5 g, 0.08 mole) in dry THF (50 ml). The temperature is kept below 5° C. After the addition is complete, the reaction mixture is stirred for 1.5 hours at room temperature.

A second Grignard solution prepared from 3-dimethylaminopropyl chloride (12 g, 0.09 mole) and magnesium turnings (3 g, 0.12 mole) in dry THF (50 ml) is added to the reaction mixture. The temperature is kept below 10° C. during the addition. The reaction is 2 hours at room temperature with stirring.

The reaction mixture is poured into ice water (100 ml) and a saturated solution of ammonium chloride (50 ml). THF is evaporated off in vacuo. Dichloromethane (100 ml) is added and the organic phase is separated and washed with water (2×50 ml) and brine (50 ml). The organic phase is extracted with 2 M HCl (2×100 ml). To the aqueous phase is added 4 M NaOH (100 ml) to give a final pH of 9 or higher. The water layer is extracted with dichloromethane (200 ml) and the organic phase is washed with water (50 ml), brine (50 ml) and dried with $MgSO_4$ (20 g). dichloromethane is evaporated off in vacuo. To the thus obtained material is added DCM (250 ml) and triethylamine (20 g, 0.2 mole). The solution is cooled to 5° C. Methanesulfonyl chloride (18 g, 0.16 mole)) is added dropwise and after addition the reaction mixture is left for one hour with stirring. The reaction mixture is washed with 0.1 M NaOH (2×100 ml) and the organic phase is dried ($MgSO_4$, 10 g) and the solvent is evaporated in vacuo. Yield: 16.5 g. 69%. $^1$H NMR (DMSO-$d_6$, 250 MHz): 1.35–1.58 (2H, m), 2.23 (2H, t, J=8 Hz), 2.50 (6H, s), 2.83 (2H, t, J=8 Hz), 2.89 (3H, s), 2.97 (3H, s), 5.13 (1H, d, J=12.5 Hz), 5.21 (1H, d, J=12.5 Hz), 7.17 (2H, t, J=8.5 Hz), 7.30–7.38 (2H, s+d, J=7.5 Hz), 7.54–7.66 (3H, dd+d, J=8.5 Hz J=6 Hz J=7.5 Hz).

The oxalate salt is precipitated from acetone.

Example 6
5-Formyl-1-(3-dimethylaminopropyl)-1-(4-fluorophenyl)-1,3-dihydroisobenzofuran The amide of Example 4 (0.025 mole) is dissolved in toluene (100 ml). The solution is cooled to 0° C. Dibal-H (30 ml, 1M solution in toluene, 0.03 mole) is added dropwise while the temperature is kept at 0° C. Cooling is removed and the solution is stirred for an additional 2 hours. Ice water (5 g) is added carefully and left with stirring for 30 min. $K_2CO_3$ (20 g) is added and stirring is continued for 10 min. The suspension is filtered and the organic phase is washed with water (30 ml). Toluene is evaporated off in vacuo and the title compound (free base form) is left as a clear oil. Yield: 7 g, 88%.

The oxalate salt is formed from acetone: DSC onset: 128° C. $^1$H NMR (DMSO-$d_6$, 250 MHz): 1.35–1.65 (2H, m), 2.24 (2H, t, J=8 Hz), 2.66 (6H, s), 3.02 (2H, t, J=8 Hz), 5.18 (1H, d, J=13 Hz), 5.28 (1H, d, J=13 Hz), 7.17 (2H, t, J=8.5 Hz), 7.60 (2H, dd, J=8.5 Hz J=6 Hz), 7.75 (1H, d, J=7.5 Hz), 7.82 (1H,s), 7.88 (1H, d, J=7.5Hz).

Anal. calcd. for $C_{20}H_{22}N_1F_1O_2$. 1.2 $C_2H_2O_4$; C, 61.79: H, 5.65: N, 3.22. Found C, 61.62: H, 5.86: N, 3.45.

Example 7

5-Formyl-1-(3-dimethylaminopropyl)-1-(4-fluorophenyl)-1,3-dihydroisobenzofuran oxime 5-Formyl-1-(3-dimethylaminopropyl)-1-(4-fluorophenyl)-1,3-dihydroisobenzofuran (33 g, 0.1 mole) is dissolved in EtOH (150 ml). Hydroxylamine, HCl (14 g, 0.2 mole) in water (150 ml) is added and pH is adjusted to pH=10 using NaOH (28% aq). The mixture left with stirring for 14 hours. EtOH is removed in vacuo and EtOAc (200 ml) and water (100 ml) is added and the phases are separated. Evaporation of the solvents from the organic phase leaves the oxime as an oil. Yield: 33 g. 96%.

$^1$H NMR (DMSO-$d_6$, 250 MHz): 1.15–1.43 (2H, m), 2.02 (6H, s), 2.15 (4H, t+t, J=7 Hz), 5.10 (1H, d, J=12.5 Hz), 5.18 (1H, d, J=12.5 Hz), 7.10–7.30 (4H, m), 7.50–7.63 (3H, m), 8.19 (1H, s), 11.34 (1H, s).

The oxalate of the title compound is crystallized from acetone. DSC: reaction onset. $^1$H NMR (DMSO-$d_6$, 250 MHz): 1.36–1.63 (2H, m), 2.20 (2H, t, J=8 Hz), 2.65 (6H, s), 3.00 (2H, t, J=8 Hz), 5.11 (1H, d, J=12.5 Hz), 5.21 (1H, d, J=12.5 Hz), 7.16 (2H, t, J=8.5 Hz), 7.45–7.63 (5H, m), 8.15 (1H, s) 9.35–10.05 (2H, broad peak).

Anal. calcd. for $C_{20}H_{23}N_2O_2F_1$. 1.05 $C_2H_2O_4$; C, 60.75: H, 5.79: N, 6.41. Found C, 60.55: H, 6.06: N, 5.93.

Example 8

1-(3-Dimethylaminopropyl)-1-(4-fluorophenyl)-1,3-dihydroisobenzofuran-5-carbonitrile, and the Oxalate Salt Thereof Method A): 5-Formyl-1-(3-dimethylaminopropyl)-1-(4-fluorophenyl)-1,3-dihydroisobenzofurane oxime, or oxalate salt, (12 g) is dissolved in acetic acid anhydride (20 ml) and pyridine (80ml). The solution is heated to reflux temperature for 2 hours. The volatile materials are evaporated off in vacuo and the remains coevaporated with toluene (2×100 ml). The thus obtained material is dissolved in acetone and oxalic acid (5 g) is added. The solution is left at 0° C. for 14 hours. Filtration yields the title compound as the hydrogen oxalate salt.

Yield: 9.6 g. 66%. DSC onset: 155° C.

Method B): 5-Formyl-1-(3-dimethylaminopropyl)-1-(4-fluorophenyl)-1,3-dihydroisobenzofurane oxime, oxalate salt (1.0 g) is suspended in toluene (10 ml). $SOCl_2$ (2 ml) is added and the mixture is heated at reflux temperature for 15 min. Evaporation of the volatile solvents in vacuo leaves an oil. The oil is taken up in toluene (10 ml) and is washed with 2 N NaOH (5 ml, aq) and water (5 ml). Evaporation of the the toluene phase leaves the title compound (free base) as an oil. Yield=0.62 g. 83%, Purity: >98.0% (hplc, peak area).

What is claimed is:

1. A method for the preparation of citalopram comprising the steps of:
 a) subjecting a compound of Formula IV:

Formula IV

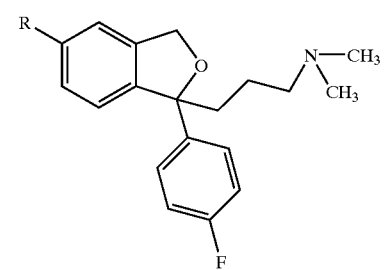

wherein R is a group:

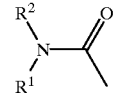

wherein $R^1$ and $R^2$ are independently selected from lower alkyl, aryl and heteroaryl, or $R^1$ and $R^2$ together with the N-atom to which they are linked form a 5- or 6-membered ring optionally comprising an S, O or N atom in addition to the N-atom to which $R^1$ and $R^2$ are attached, or R is 4,5-dihydro-1,3-oxazol-2-yl optionally substituted in the 4- and or 5-position with one or more lower alkyl, aryl or heteroaryl groups to reductive hydrolysis, and b) converting the resulting 5-formyl compound of Formula V:

Formula V

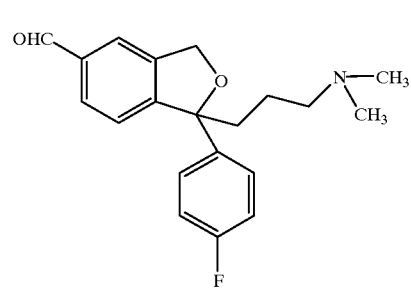

to the corresponding 5-cyano compound, citalopram:

Formula I

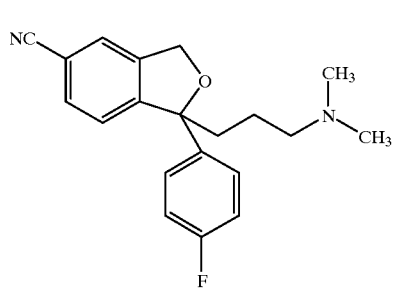

which is isolated as the base or a pharmaceutically acceptable salt thereof.

2. The method of claim 1 wherein the conversion of the 5-formyl compound of Formula V to citalopram is carried out by conversion of the formyl group by reaction with a reagent $R^3$—X—$NH_2$ wherein $R^3$ is hydrogen, lower alkyl, aryl or heteroaryl and X is O, N or S, followed by dehydration with a dehydrating agent.

3. The method of claim 1 wherein R is a group

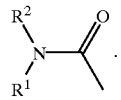

4. The method of claim 3 wherein $R^1$ and $R^2$ are lower alkyl or $R^1$ and $R^2$ with the N-atom to which they are linked form a 5- or 6-membered ring optionally comprising an S, O or N atom in addition to the N-atom to which $R^1$ and $R^2$ are attached.

5. The method of claim 4 wherein $R^1$ and $R^2$ are both methyl or $R^1$ and $R^2$ together with the N-atom to which they are linked form a morpholinyl group.

6. The method of claim 1 wherein R is an optionally substituted 4,5-dihydro-1,3-oxazol-2-yl group.

7. The method of claim 6 wherein R is 4,5-dihydro-4,4,-dimethyl-1,3-oxazol-2-yl.

8. The method of claim 1 wherein the intermediate of Formula IV is prepared by ring closure of the corresponding compound of Formula VI:

Formula VI

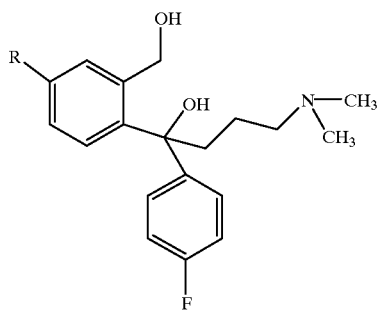

wherein R is as defined in claim 1.

9. The method of claim 8 wherein the compound of Formula VI is obtained from the corresponding 5-substituted phthalide derivative by reaction with a Grignard reagent of 4-halogen-fluorophenyl followed by reaction with a Grignard reagent of 3-halogen-N,N-dimethyl-propylamine.

10. The method of claim 8 wherein the compound of Formula VI is prepared from 4-dimethylamino-1-(4-fluorophenyl)-butan-1-one by Grignard reaction with a protected 2-(hydroxymethyl)-4-(1,3-oxazol-2-yl)-phenyl magnesium halogenide derivative.

11. The method of claim 8 wherein the ring closure of the compound of Formula VI is effected by acidic ring closure performed by an inorganic acid or an organic acid.

12. The method of claim 11 wherein the acidic ring closure is performed by an inorganic acid selected from the group consisting of sulfuric acid or phosphoric acid.

13. The method of claim 11 wherein the acidic ring closure is performed by an organic acid selected from the group consisting of methylsulfonic acid, p-toluenesulfonic acid or trifluoroacetic acid.

14. The method of claim 8 wherein the ring closure of the compound of Formula VI is performed by a basic ring closure via a labile ester.

15. The method of claim 14 wherein the ring closure via a labile ester is performed with simultaneous esterification and addition of a base.

16. The method of claim 15 wherein the labile ester is a methane sulfonyl, p-toluene sulfonyl, 10-camphorsulfonyl, trifluoroacetyl or trifluoromethanesulfonyl ester and the base is triethyl amine, dimethylaniline or pyridine.

17. The method of claim 11 wherein, before further reaction, the intermediate of Formula VI is separated into its enantiomers, thereby obtaining the enantiomer giving S-citalopram.

18. A compound of Formula V:

Formula V

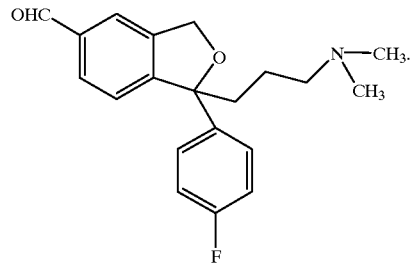

19. A compound of Formula IV:

Formula IV

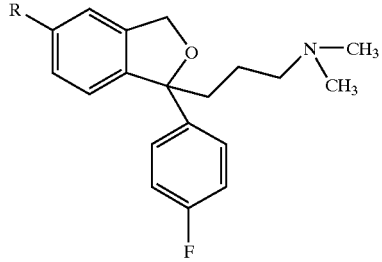

wherein R is a group:

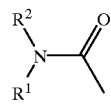

wherein $R^1$ and $R^2$ are independently selected from lower alkyl, aryl and heteroaryl, or R and $R^2$ together with the N-atom to which they are linked form a 5- or -6-membered ring optionally comprising an S, O or N atom in addition to the N-atom to which $R^1$ and $R^2$ are attached, or R is 4,5-dihydro-1,3-oxazol-2-yl optionally substituted in the 4- and or 5-position with one or more lower alkyl, aryl or heteroaryl groups.

20. A compound of Formula V:

Formula V

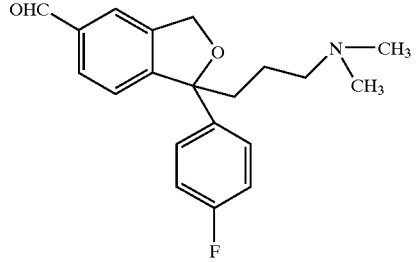

or an acid addition salt thereof.

21. The oxalate salt of the compound of Formula V:

Formula V

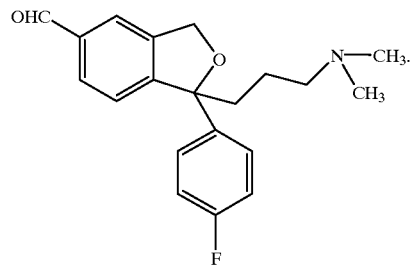

* * * * *